United States Patent [19]

Hill et al.

[11] Patent Number: 4,911,927
[45] Date of Patent: Mar. 27, 1990

[54] METHOD AND APPARATUS FOR ADDING CHEMOTHERAPEUTIC AGENTS TO DENTAL FLOSS

[76] Inventors: Ira D. Hill, Clay Ct., Locust, N.J. 07760; Robert D. White, 65 Glen Gray Rd., Oakland, N.J. 07436

[21] Appl. No.: 270,562

[22] Filed: Nov. 14, 1988

[51] Int. Cl.⁴ .............................................. A61K 9/70
[52] U.S. Cl. .................................... 424/443; 132/323; 427/2; 427/175
[58] Field of Search ..................... 424/443; 427/2, 175; 132/323

[56] References Cited

U.S. PATENT DOCUMENTS 4,029,113  6/1977  Guyton ............................... 132/321
4,610,872  9/1986  Lynch ..................................... 424/49

Primary Examiner—Thurman K. Page
Attorney, Agent, or Firm—Ernest V. Linek

[57] ABSTRACT

A method and apparatus for the manufacture of various dental flosses containing chemotherapeutic preparations which are releasable during flossing.

17 Claims, 3 Drawing Sheets

METHOD AND APPARATUS FOR ADDING CHEMOTHERAPEUTIC AGENTS TO DENTAL FLOSS

FIELD OF THE INVENTION

The present invention relates to oral hygiene and specifically to a method of manufacturing innovative dental floss with improved cleaning, conditioning and therapeutic properties.

BACKGROUND OF THE INVENTION

Proper use of dental floss is necessary to clean the considerable area on the interproximal surfaces of teeth, which cannot be reached by the bristles of a toothbrush.

The purpose of dental floss is:

1. to dislodge and remove any decomposing food material that has accumulated at the interproximal surfaces that cannot be removed by brushing, and
2. to dislodge and remove as much as possible the growth of bacterial material (plaque) upon the teeth or the superimposed calculus that has accumulated there since the previous cleaning. Plaque is discussed below.

The concept of the use of dental floss for cleansing interproximal spaces appears to have been introduced by Parmly in 1819. Parmly suggested the use of waxed silk to clean teeth of persons subject to gingival inflammation. Numerous types of floss were developed and used for cleaning, until finally in 1948 Bass established the optimum characteristics of dental floss. (Dental Items of Interest, 1948; 70: 921-34).

Surprisingly, floss marketers have ignored Bass for the past 40 years. Bass warned that dental floss treated with sizing, binders and/or wax produces a "cord" effect which reduces flossing efficiency dramatically. Almost all floss sold today including unwaxed floss contains binders and/or sizing substances. These "sticky" substances are used to keep the floss twists from unwinding during use and to keep the floss turns from falling off a spool during dispensing by holding the floss together. Additionally, most floss sold at retail today is also "waxed" to assist penetration of interproximal regions; as the "cord" effect described by Bass makes the floss bundle difficult to force between closely spaced teeth.

The optimum characteristics of dental floss as described by Bass in 1948 are ignored by today's flosses. Specifically, Bass suggests that these waxed and sized flosses produce the "cord" effect discussed above as distinguished from the "spread effect" of unwaxed, unsized floss which flattens out and widens, with the filaments spread out. The potential for separate mechanical action of spread out filaments is nullified by this "cord" effect, as are the spaces between the filaments, which according to Bass are necessary to receive, hold and remove the microscopic material dislodged during flossing. Thus, the mechanical cleaning attributed to spread filaments and essentially all of the evacuation of microscopic materials from the interproximal spaces by entrapment is impaired or sacrificed with waxed and/or sized flosses, because of this "cord" effect.

As an alternative to sizing, binders, wax etc. Bass suggests "steamset" to set the twist in dental floss so that the floss will not untwist during use. Commercial floss twisters and floss spoolers, opted to use various binders and sizing materials instead. These "sticky" substances facilitate floss handling, keep the floss from untwisting during use, and keep the floss from falling off the spool. Although steamset floss does not untwist during use, absent sticky substances, it does unravel off the spool during dispensing and during spooling. Thus, the optimum floss described by Bass could not be manufactured commercially in 1948, so apparently, water insoluble binders, sizing and wax were adopted early on and continue up to the present.

From 1960 thru 1982, numerous clinical studies reported that there is no clinical difference as to plaque removal and gingivitis scores between waxed and unwaxed dental floss. Note, both are "cord" flosses and contain sizing, binders etc. These studies also confirmed that waxed and unwaxed floss are approximately 50% effective with respect to plaque removal and gingivitis scores. Thus the "cord" effect severely restricts efficiency of flossing.

O'Leary in 1970, and Hill et al in 1973, found no difference in the interproximal cleansing properties of waxed or unwaxed dental floss. This was reconfirmed in 1982 by Lobene et al who showed no significant clinical difference on plaque and gingivitis scores. Similar results, i.e. no clinical difference between waxed and unwaxed floss with respect to reduced gingival inflammation were shown by Finkelstein in 1979. No differences in gingival health were shown by Wunderlich in 1981. No differences in plaque removal were reported by Schmidt et al in 1981 with flosses of various types. Stevens, 1980, studied floss with variable diameters and showed no difference in plaque and gingival health. Carter et al 1975, studied professional and self administered waxed and unwaxed floss, both significantly reduced gingival bleeding of interproximal and gingival sulci. Unwaxed floss appeared slightly, but not significantly more effective.

In view of this clinical work, it is not surprising that most of the dental floss sold today is bonded and/or waxed. The "bonding" in the yarn industry today is used more to facilitate processing and production during floss manufacture and packaging than for "flossing" reasons. Since clinical tests show no difference between waxed and unwaxed floss (both unfortunately are "bonded") the floss industry has been comfortable with the yarn industry's propensity to use bonding agents in floss.

Today there are three basic nylon strand constructions approved by the FDA for flossing. These are 140 denier (68 filament), 100 denier (34 filament), and 70 denier (34 filament). Analysis of the commercial flosses sold worldwide show that almost all flosses available are twisted in generally the same manner, contain bonding agents, and are constructed by twisting several (6-10) strands selected from one of these three strand types.

Almost 100% of the floss sold today is manufactured by "yarn" manufacturers with little consideration given to the influence of twisting of floss construction on cleaning etc.

The simple removal of binders, to allow the floss strands to spread out, introduces a "user-unfriendly" effect which reduces the value Bass described. Commercial flosses with little or no binders are notorious for frustrating flossers with their tendency to fray, break etc. The removal of binders requires adjuncts (lubricants, etc) to reduce snagging, fraying etc.

In view of the foregoing, it is not surprising that shred resistant floss has been the basic claim of some floss marketers. The most recent introduction of a Goretex type floss, with it's monofilament construction, should prove to be the ultimate shred resistant floss. Historically, the typical response to shredding was to develop a "tighter" bonded and smaller diameter floss that did not spread out and did not shred. Waxing was also an option. It is not difficult to see how the "ultimate cord", i.e. monofilament construction, evolved from this approach. The monofilament floss is reported to be easier to use than traditional bonded flosses.

Somehow it has become generally accepted throughout the oral care community today that:

1. the daily mechanical disruption and removal of dental plaque with a standard bonded dental floss is a very effective method of interproximal plaque control. and 2. it would be difficult to demonstrate clinical superiority over the standard commercial flosses.

This conclusion contradicts the mediocre plaque and gingivitis control effect of standard floss as reported consistently in the literature, to wit:

1. The literature has repeatedly documented that gingivitis scores flatten out after 4 weeks of flossing with scores routinely in the 60's. See Lobene et al and other waxed vs unwaxed dental floss studies.

2. Many researchers report that the best floss in the hands of experts will only remove 50 to 60% of the interproximal plaque.

3. Keene in 1974, reported that "... ordinary waxed dental floss was neither an efficient debriding agent nor an effective tool for delivery of the test agents to the interproximal sites", and 4. Additionally, Finkelstein and Grossman, Hill et al, Carter et al, Wunderlich et al, Schmid et al, Lamberts et al and Stevens each showed plaque reductions and/or improved gingivitis or improved gingival health with flossing. These results were comparable to Lobene et al, 50 to 60% effective, and leave room for substantial improvement.

There is, therefore a definite need in the art for an improved dental floss, to clean, condition and treat the surfaces flossed.

BRIEF DESCRIPTION OF THE INVENTION

Proper flossing procedure as recently described in "Dental Health Adviser" includes: "slide it (floss) between your teeth using a gentle sawing motion" and "scrape the sides of your teeth with an up and down motion". It has now been found that this type of mechanical action can be supplemented by the release of surfactants from the floss into the interproximal region. These released surfactants are readily solubilized in saliva and interproximal fluids to produce a detersive effect in the interproximal region during flossing. Foaming of the surfactant is avoided with the use of silicone conditioners, thus optimizing this detersive effect. The surface active properties of the surfactant and silicone presented interproximally, not only assist in cleaning debris and plaque from the interproximal sites, and condition teeth and gums but they also alter the surface tension of the paste remaining; as well as disrupting plaque matrix reattachment. The method of treating the oral cavity with these flosses is described in our application Ser. No. 270,162 filed Nov. 14, 1988, the disclosure of which is incorporated by reference.

This improved lifting of debris, plaque and soil from the interproximal spaces with surfactants is further enhanced by the use of unbonded floss strands which spread out and follow the contours of the teeth during flossing/cleaning. This improved mechanical cleaning is further supplemented with various insoluble abrasives released interproximally from the floss during flossing. This combination of abrasive, surfactant and mechanical action is more efficient than mechanical action alone with waxed floss.

The following features of the present invention characterize the surfactant/silicone/abrasive enhancement effect produced when flossing interproximally:

1. Rapid release of substantial quantities of saliva soluble surfactant, silicone and abrasive when the floss is pulled across tooth surfaces. The construction of the floss, the use of unbonded floss, the absence of wax and a unique loading process which encourages the floss to open up and release the load during flossing.

2. Rapid solubilization of a surfactant with high detergency, and saliva solubility, combined with simethicone produce excellent detersive results with no foaming, and 3. The tendency to use "fresh" loaded floss is for each interproximal site flossed. The addition of hedonic substances, flavor, oils, silicone, "mouth-feel" affecting gums, etc. to the load encourage the flosser to unwind fresh floss prior to flossing a new site. Thus, the flosser is hedonically driven to use fresh floss with the present invention.

The potential development of hedonically superior flosses has been surprisingly restricted and may be a critical factor in the failure of flossing to penetrate more than about 10% of the adult U.S. market.

The superior flavored flosses available commercially are based on "encapsulated flavor" technology where the flavors are delivered in a spray dried matrix form to the bonded floss. See U.S. Pat. No. 3,943,949. These flavored flosses are available waxed or unwaxed. Less effective application and retention of flavor is also commercially achieved by direct contact of the floss with flavor oil/solvent solutions. The inherent limitations of the encapsulated flavored flosses are evident when these products are compared to "flavor oil in a solidified melt emulsion" treated flosses of the present invention.

Other hedonic areas critical to a positive consumer response towards flossing such as "mouth feel" have not been addressed by current floss products.

It is generally accepted that floss is not a "user-friendly" product, i.e. it is difficult to do. It causes pain and bleeding and it results in a bad taste in the mouth. Most market researchers agree that anything that can be done to make flossing more positive should be implemented to encourage more frequent flossing and more wide spread floss use. The addition to floss of: full spectrum flavor oils, mouth conditioning substances such as silicones, and cleaners and abrasives that leave a "clean, just brushed feeling" as taught by the present invention are all sources of positive feed back to the flosser that would be considered encouraging and supportive. To achieve these requires basic changes in floss construction, physical chemistry of floss additives and new "loading" technology that goes beyond waxing and the "yarn" (cord) approach to floss construction. These are described in our application Ser. Nos. 270,562 and 270,544 filed Nov. 14, 1988, the disclosures of which are incorporated by reference.

With the advent of "loading actives" into floss for release during flossing as discussed below, the opportunity is available to include densensitizing agents into the load to minimize flossing pain and discomfort. Typically, desensitizing agents such as strontium chloride are used in dentifrices for "sensitive" teeth. These substances produce a comparable effect when released interproximally from the floss of the invention. This desensitizing effect further improves the overall hedonics of the floss of the invention. Examples of floss of the invention with desensitisers are described below.

Analysis of current waxed floss users shows a consistent tendency to "re-use the floss" and not to use a fresh piece of floss for each interproximal site. The spent "waxed" floss, under close inspection shows little entrapped, dislodged microscopic particles because of the "cord" effect.

In contrast, as noted above users of the floss of the present invention show a consistent tendency to use "fresh" floss for each new interproximal region. Additionally, the "spent" floss of the present invention contains entrapped substances which can be observed by the flosser. This tends to motivate the use of fresh floss as well. The mouth feel and taste imparted by the floss reinforces that the floss is working by leaving a clean, fresh feeling in the mouth.

Surprisingly, when the substances of the present invention are added to floss strands they perform one critical function of the standard size or binder in that they keep the floss from untwisting during use and impart the "stickiness" necessary to allow the floss to be spooled and dispensed without unravelling. However, because of the chemistry of these substances and the loading process used; contrary to the bonded or waxed floss, the loaded floss of the present invention spreads out during use to obtain the separate mechanical action of the many filaments.

This spreading out during flossing, also triggers the release mechanism which discharges most of the load interproximally during flossing, i.e. up to about 80% by weight. The surfactant/silicone/abrasive mixture thus, released is readily solubilized in the saliva and other fluids present. This solubilized mixture responds to the separate mechanical action of the floss filaments resulting in a nonfoaming detersive effect in the interproximal space.

Release of the load leaves spaces in the floss which tend to take up and hold some of the microscopic substances dislodged during flossing. These "captured" substances can be easily observed in the "spent" floss.

The floss of the invention is preferably a nylon dental floss that has been processed to load into it up to about 80 mg/yd of a proprietary cleaning and plaque fighting formulation. Up to about 80% of this load is released onto interproximal and subgingival sites during flossing, i.e. up to about 64 mg/yd. This release of surfactant cleansing in the area flossed is not available with flosses sold today. The flosses of the invention show superior cleaning over waxed or unwaxed commercial flosses.

Additionally, the floss of the invention can contain therapeutic substances for release at concentrations up to 40 mg/yd. When these substances are included in the load they are released onto those interproximal and subgingival sites which cannot be reached by rinsing or brushing. This interproximal release of substances in these concentrations is unique, improves plaque control and gingivitis scores and is described in more detail in copending applications.

Most authorities agree that control of periodontal diseases requires:
1. regular disruption of subgingival microflora, and
2. regular removal of supragingival plaque.

Many rinses and dentifrices claim supragingival control of plaque and/or tartar. None are proven effective subgingivally and have limited supragingival effect interproximately. Floss has been proven to have some subgingival mechanical disruption value, but no chemotherapeutic value subgingivally or supragingivally.

In contrast, regular flossing with the floss of the invention provides a unique combination of mechanical action, detersive action, surface modification and chemotherapy which results in:
 a. disruption of subgingival microflora, and
 b. removal of interproximal supragingival plaque.

Subgingival chemotherapeutic disruption of microflora is achieved by the unique combination of:
 a. chemical cleansing with surfactants released from the floss of the invention,
 b. prolonged modification of the surface chemistry of the microflora by the coating materials released, e.g. silicones, released from the floss, and
 c. alteration of microflora with various actives contained in the load and released during flossing.

Subgingival mechanical disruption of microflora is achieved by the unique combination of:
 a. physical disruption by the "spread-out", lubricated floss fibers,
 b. abrasive disruption with abrasives released from floss including: silica, dicalcium phosphate, pyrophosphates etc, at concentrations up to 40 mg/yd; and
 c. surfactant disruption resulting from the release of surfactants during flossing.

Chemotherapeutic removal of supragingival plaque is achieved by the unique combination of:
 a. chemical cleansing with surfactants released from the floss,
 b. modification of the surface chemistry of the plaque with coating materials e.g. silicones, and
 c. alteration of the plaque with various actives contained in the load and released during flossing including: tetrasodium pyrophosphate, tetrapotassium pyrophosphate etc.

Mechanical removal of supragingival plaque is achieved by the unique combination of:
 a. physical removal by the unbonded, spread out, lubricated floss fibers,
 b. abrasive removal by the abrasives released from the floss including: silica, dicalcium phosphate, pyrophosphates etc, and
 c. cleansing resulting from the release of surfactants during flossing.

Plaque is a microbially formed coating on tooth surfaces, bound together by natural polymers, (mucopolysaccharides) formed by microbial action on salivary fluids, cell debris, food remnants, sugars and starches in the mouth. Embedded in this polymer matrix are the bacteria normal to the oral cavity but, when trapped against tooth surfaces and protected by the matrix from easy removal, are in excellent position for "mischief". Most dental texts implicate plaque in the formation of caries, or tooth decay. In addition, these embedded bacteria release toxins that cause gingivitis, bleeding and swelling of the gums. Gingivitis can lead to periodontitis in which gums recede, pockets of infection form and teeth loosen.

Plaque formation is an ongoing process. Various gel and paste dentifrice preparations, mouth rinse and mouth prerinse preparations, make plaque and/or tartar control claims. One disadvantage of these preparations is that only a relatively short time during which the teeth are being cleaned or the mouth is being rinsed is available for these preparations to take effect. These preparations generally have little residual effect on plaque formation. Further these rinses are limited to supragingival plaque and tartar control and have little access to the critical interproximal areas. In contrast, the floss of the present invention releases substances interproximally and subgingivally. Additionally, some of these preparations such as mouth rinses and prerinses contain various antimicrobial substances which may alter the critically balanced microflora of the mouth. Generally, these substances are introduced into the oral cavity in large quantities due to the dilute nature of the delivery vehicle.

Effective oral hygiene requires that three control elements be maintained by the individiual:

1. Physical removal of stains, plaque and tartar. This is accomplished in the strongest sense by scraping and abrasion in the dentist's office. Self administered procedures are required frequently between visits and range from tooth brushing with an appropriate abrasive toothpaste through flossing and water jet action down to certain abrasive foods and even the action of the tongue against tooth surfaces.

2. Surfactant Cleansing. This is required to remove: food debris and staining substances before they adhere to the tooth surfaces; normal dead cellular (epithelial) material which is continually sloughed off from the surfaces of the oral cavity and microbial degradation products derived from all of the above. Besides the obvious hygenic and health benefits related to simple cleanliness provided by surfactants, there is an important cosmetic and sense-of-well-being benefit provided by surfactant cleansing. Research has shown that the primary source of bad breath is the retention and subsequent degradation of dead cellular material sloughed off continuously by the normal, healthy mouth.

3. Frequency of Cleansing. This is perhaps the most difficult to provide in today's fast-paced work and social environment. Most people recognize that their teeth should be brushed at least 3 times a day and flossed at least once a day. The simple fact is that most of the population brush once a day, some brush morning and evening, but precious few carry toothbrush and dentifrice to use the other three or four times a day for optimal oral hygiene. Consumer research suggests that the population brushes an average of 1.3 times a day. Most surprising, less than 10% of adults floss regularly. Reasons offered for not flossing; difficult to do, painful, not effective and leaves a bad taste. Overall, floss is not a "consumer friendly" product.

Since plaque is regarded by most of the dental profession as a causitive agent leading to various dental pathologies discussed in detail below, there is considerable desire by most consumers to remove or prevent the formation of plaque on a daily basis.

There are four oral care techniques which address the problem of plaque: abrasion, anti-microbial agents, removal of precursors to plaque, and altering the attachment of plaque to a surface.

1. Abrasive removal of the plaque film, once it has firmly adhered to the tooth surface, is the only totally effective cleansing mechanism. Again, professional dental hygiene is most effective, but recently, a number of special abrasive toothpastes have been accepted by dental organizations for partially removing supragingival adhered plaque and the tartar which subsequently forms from the plaque. Heretofore, interproximal plaque could only be removed by mechanical means such as flossing and/or by use of appropriately shaped dental stimulators. Dental stimulators containing the substances of the invention are disclosed in our application Ser. No. 270,156, filed Nov. 14, 1988, the disclosure which is incorporated by reference.

2. Antimicrobial action can affect plaque formation in two ways, (a) reducing the number of bacteria in the mouth which form the mucopolysaccharides and (b) killing those bacteria trapped in the film to prevent further growth and metabolism. However, the medical and dental community is divided about the advisability of frequent use of antimicrobial agents in the mouth in rinses or prerinses, especially the most effective ones, except under strict supervision of licensed practitioners. There is a number of reasons given, but one concern is that such materials would upset the ecological balance of the mouth. A balanced, "friendly" microbial population is necessary to prevent pathogenic organisms from taking over. By contrast, delivery of anti-microbial agents directly to the critical sites would more effectively treat the disease or predisease condition with localized concentrations. The microflora of these sites could be altered with appropriate substantive antimicrobials. Obviously, a more effective cleansing and physical removal, such as provided by the present invention, reduces even further the required total concentrations of anti-microbials required to produce effacacy. These methods are described in our applications 270,167, 270,161, 270,353, 270,166 and 270,164, all filed Nov. 14, 1988, the disclosures of which are incorporated by reference.

3. Removal of plaque precursors requires the reduction of food sources and building blocks required for the bacteria to synthesize the mucopolysaccharides which polymerize into the plaque film. Going far back into the chain of events leading to plaque formation and interrupting the chain has much to commend it as a sound oral hygiene strategy. However, for this technique to be effective, the plaque building blocks must be interrupted periodically throughout the mouth, especially at the site of plaque buildup and if possible just below the tooth-gum interface and interproximally. Such disruption is described in copending applications Ser. Nos. 927,752 and 927,805 filed Nov. 7, 1986. Most other oral hygiene preparations described above fall short on "frequency-of-use" basis, abrasion and cleaning. For reference, see, L. Menaker, "The Biologic Basis of Dental Caries", Chapters, 5, 11, 12, 14, 16 and 18, Harper and Row (1980).

4. As to altering attachment of plaque, it has now been found that the cleaning and coating compositions described below can be incorporated into dental floss of specified construction at surprisingly high concentrations; considering that the compositions of the invention are not soluble in the floss. Secondly, floss so treated will "release" these compositions during flossing and chemically cleanse the area of plaque and plaque precoursors, bacteria, etc., while coating teeth and gum surfaces with a plaque matrix disrupting substance. The release of these substances is particularly effective in disrupting, for prolonged periods, the plaque matrix on these interproximal sites. The cleaning that results from the compositions released from the floss also takes place on those interproximal surfaces brushing does not reach. This chemical cleansing and matrix disruption adds a new dimension to flossing beyond the physical removal of debris from these surfaces.

DETAILED DESCRIPTION OF THE INVENTION

The present invention comprises:
a multi strand dental floss containing, an ingestible, nonfoaming, plaque disrupting composition comprising cleaners and coating substances dispersable in said cleaners wherein:

a. the multi-strand floss:
1. contains from between 2 and 12 strands,
2. has a denier between about 300 and about 1200, and
3. contains between about 100 and about 800 filaments.

In a preferred embodiment of the invention the floss is nylon, contains between 4 and 8 strands, with a denier between about 500 and 1000 and contains between about 200 and 600 filaments. In a particulary preferred embodiment of the invention the floss is nylon, contains 6 strands, has a denier of about 840 and has approximately 408 filaments.

b. the strands include natural and/or synthetic fibers and mixtures thereof including cotton, silk, polyester and nylon.

c. the cleaners include: surfactants and emulsifiers such as:
sodium lauryl sulfate,
sodium lauroyl sarcosinate,
polyethyleneglycol stearate,
polyethyleneglycol monostearate,
coconut monoglyceride sulfonates,
soap powder,
sodium alkyl sulfates,
sodium alkyl sulfoaoetates,
alkyl polyglycol ether carboxylates such as those described in U.S. Pat. No. 4,130,636
polyoxyethylene derivatives of sorbitan esters, such as those described in U.S. Pat. Nos. 3,639,563; 3,947,570,
propoxylated cetyl alcohol as described in U.S. Pat. No. 2,677,700; and Preferred commercially available substances which include:
polyoxyethylene, polyoxybutylene block copolymers such as Pluronic F108, and F127 (BASF) and polysorbates such as Tween 40, and 80, (Hercules).

Particularly preferred surfactants include block copolymers comprising a cogeneric mixture of conjugated polyoxybutylene and polyoxyethylene compounds having as a hydrophobe, a polyoxybutylene polymer of at least 1200 molecular weight; such as described in U.S. Pat. Nos. 4,343,785, 4,465,663; 4,511,563 and 4,476,107, and d. the coating substances can be characterized as follows, they:
1. suppress the tendency of the surfactant cleaners that are present to foam,
2. are safely ingestible at the concentrations used,
3. have an affinity for mouth and teeth surfaces,
4. are neutral, inert and do not support biological activity,
5. modify the surface energy properties of oral cavity surfaces such that it is more difficult for food particles, cellular debris and vairous plaque precursors and formers to attach to these oral cavity surfaces,
6. form a fugitive thin, transparent coating that does not build up on oral cavity surfaces and is removed by the normal clearing and flushing action of the mouth,
7. impart a pleasant "smooth" feeling to the surfaces of the mouth, gums and teeth, and
8. retain various flavors, sweetners and pharmacologically preparations active on surfaces of the mouth imparting an unexpected prolonged effect of the pharmacologically active substances as well as prolonged flavor perception, and e. The coating substances include: various silicones, long chain hydrocarbons, carbowaxes and polymers such as:
silicone glycol co-polymers,
polydimethyl siloxanes,
long chain hydrocarbons, especially normal paraffins having a chain length of 16 carbons atoms or greater, paraffins with several loci of branching and unsaturation, where the extent of such branching and unsaturation does not create unacceptable toxicity nor lower the solidification point below body temperature, Carbowaxes (polyethylene glycols), and polymers which have limited solubility in ethanol and water solutions where the ethanol: water ratio is greater than 0.3:1 but have essentially no solubility in water or saliva at lower ratios.

The combination of certain cleaners with certain coating substances, wherein the latter is inherently insoluble in the former, in a treated dental floss is novel. The prolonged plaque matrix disruption so obtained with a floss containing this combination in the mouth, is novel. Furthermore, the cleaner, coating substance, and saliva or gingival crevice fluid mixture obtained when the compositions are released in the mouth are ingestible and can be pleasantly swallowed, which further distinguishes it from typical oral cleaning compositions used with a toothbrush and most rinses and prerinses. For example, unlike typical cleaners used in dentifrice pastes, the cleaners of the present invention do not fill the mouth with foam and can be pleasantly swallowed which is necessary for those flosses loaded with substantial quantities of releasable materials.

The compositions released from the floss during flossing can disrupt plaque formation without resort to antimicrobial ingredients. The various surfaces of teeth and gums are coated with a smooth thin film released from the floss which disrupts plaque formation. These coatings remain in the interdontal spaces for extended periods and prolong this disruption effect on plaque matrix formation.

Alternatively, for those useful embodiments of the invention where specific localized anti-microbial ingredients are therapeutically desirable, these compositions provide an excellent carrier. These compositions are described in our applications Ser. Nos. 270,163, 270,723, 270,132, 270,167 and 270,135, all filed Nov. 14, 1988, the disclosures of which are incorporated by reference.

A review of the construction of the floss of the present invention shows that the compositions of the invention are contained essentially in the interstitial spaces between the fibers of the floss with minimum composition on the outer surface of the floss. This internal loading of the compositions is achieved by opening up the floss fibers during manufacturing and introducing a melt-emulsion of the compositions of the invention into the space around the opened fibers. The manufacturing process of the invention is discussed in our copending application entitled METHOD AND APPARATUS FOR ADDING CHEMOTHERAPEUTIC AGENTS TO DENTAL FLOSS, Attorney Docket No. 38,343, filed November 14, 1988, the disclosure of which is hereby incorporated herein by reference of floss construction on loading the compositions into the floss is described in Table I below and in our copending application Ser. No. 270,544 entitled DENTAL FLOSS, Attorney Docket No. 38,342, filed November 14, 1988, the disclosure of which is hereby incorporated herein by reference.

The floss of the present invention is unique in its capacity to release the "loaded" compositions of the invention interproximally. Unexpectedly, the property of releasing these compositions correlates with the opening up and/or flattening of the treated floss strands during flossing. This tendency of the loaded floss of the invention to open up and flatten out during flossing allows the floss fibers:

a. to pass easily between teeth which are so closely spaced as to make insertion of typical floss difficult and painful, b. to conform to the surface of the teeth, c. to fit under the gum line at the gingival margin, and d. to slip into subgingival areas inorder to dislodge plaque bacteria, microflora etc. Historically, plaque, bacteria, pathogenic bacterial plaque etc collect around the gum line and in various shallow pockets that form in this area. The subgingival plaque, bacteria, microflora etc requires regular disruption to control periodontal diseases.

As discussed above, floss has generally been waxed or bonded to reduce shredding. Such treatment results in the floss tending to hold its shape during flossing which results in the floss generally not flattening out, with less than optimum conformation to teeth surfaces and interproximal surfaces. Thus, it is difficult to reach those remote interproximal areas without risk of pain and/or damaging delicate gum tissue. In contrast, the loaded floss of the invention, opens up tends to conform to surfaces and releases the loaded substances interproximally during flossing. This release mechanism results in:

1. the floss strands which are lubricated flattening to reduce shredding and minimize stripping of the load prior to reaching the interproximal sites;

2. the floss strands flattening and conforming to the surfaces over which they are worked and reaching most remote interproximal surfaces;

3. the floss strands continuing to release the loaded substances during flossing as the floss is moved over teeth, under the gum line and over the interproximal surfaces; and 4. the floss being easier to manipulate over the interproximal sites and near the gingival margin of the teeth where meticulous oral hygiene has been impaired heretofore. These are historically the most bleeding-prone areas of the mouth because heretofore they have been the most difficult to keep plaque free.

5. Finally, the flattening, conforming and lubricating properties of the floss of this invention makes it much more pleasant to use, replacing the frequently experienced pain and bleeding attendant with use of ordinary floss with a hedonically positive experience.

Thus, the release mechanism of the floss of the present invention allows the floss to reach the interproximal sites and physically remove plaque, while at the same time releasing the compositions of the invention interproximally to assist in cleaning and/or treating these interproximal sites. This releasing of the compositions was quantified as follows:

Floss described in Example 39 of Table IV containing 40 mg of load/yd was cut into 10, one yard lengths. The floss sections were dried at 104° F. for two hours and weighed. Unloaded floss was similarly heated and weighed. Two individuals flossed with five pieces each of the treated floss and with the unloaded floss. Both types of floss were again dried at 104° F. for two hours and reweighed. The average quantity of loaded actives released was established at 26 mg/yd with no significant variation between individuals or between pieces of floss.

The "load" of the compositions of the invention into the interstitial spaces between floss fibers also provides a suitable vehicle for effectively delivering other therapeutic substances to the interproximal sites. The load can include very small quantities (say 100 units per yard in the case of very active antibiotics) to large amounts (up to 60% by weight of anti tartar or other chemicals requiring mass action) across a wide variety of therapeutic substances. Thus, chemotherapeutic treatment of interproximal sites can also be achieved.

For example, specific bacterial diseases in the oral cavity can be more effectively treated if various antibiotics can be introduced topically to specific interproximal sites. These include: penicillin, polymixinB, vancomycin, kanamycin, erythromycin, niddamycin, metronidazole, and spiromycin which can be included in the compositions of the invention and loaded into a chemotherapeutic floss of the invention. Floss of the invention containing tetracycline is described in our copending application entitled DENTAL FLOSS WITH TETRACYCLINE, Attorney Docket No. 38,345, filed November 14, 1988, the disclosure of which is hereby incorporated herein by reference.

The topical application of various antibiotics to interproximal sites as well as subgingivally is preferred over "systemic" treatments with these substances. That is, the risk of adverse side reactions to the patient which accompanies most ingested systemic antimicrobials is reduced substantially. In addition, application of the antimicrobial to specific infected areas can be achieved with a higher frequency, topically than systemically. This assures higher antibiotic concentrations at the site(s) of infection and a higher incidence of effectiveness in a shorter period of time. See Goodson Implant references 1979 to 1988.

Additionally, various chemical agents can be added to the floss as antiplaque/antigingivitis agents including:

a. antiplaque and antitartar substances such as the tetrasodium or tetrapotassium pyrophosphates and zinc chloride, b. first generation agents which are antibacterial agents with limited substantivity such as oxygenating compounds, quaternary ammonium compounds, phenolic compounds and plant alkaloids such as sanguinarine, and c. second generation agents which are antibacterial agents with substantivity such as chlorhexidine, either free base or as the gluconate or other suitable salt, alexidine, octenidine and stannous fluoride. Stannous fluoride and chlorhexidine antimicrobials in the various flosses of the present invention are described in our copending applications entitled DENTAL FLOSS WITH STABILIZED STANNOUS FLUORIDE and DENTAL FLOSS WITH CHLORHEXIDINE, Attorney Docket Nos. 38,346 and 38,347 respectively, filed November 14, 1988, the disclosures of which are hereby incorporated herein by reference.

The loaded floss of the invention containing various antimicrobial substances offers the opportunity to disrupt subgingival microflora and limit regrowth while also controlling supragingival plaque. The release interproximally and subgingivally of substantive chemotherapeutic antimicrobials and the plaque disrupting compositions of the invention from the floss of the invention tends to:

a. disrupt or eliminate supragingival plaque, and pathogenic subgingival flora, and b. alter the environment interproximally and subgingivally sufficiently to prevent regrowth of disease associated microorganisms. The resulting control of plaque quantity and the periodontopathic microorganisms in plaque should help control gingivitis. Various methods of treating the oral cavity with flosses of the present invention are described our application Ser. Nos. 270,162, 270,161, 270,353, 270,166 and 270,164, all filed Nov. 14, 1988, the disclosures of which are incorporated by reference.

The first generation agents suitable for use in the floss of the present invention include:

1. quaternary ammonium compounds such as benzethonium chloride, cetylpyridinium chloride, 2. phenolic compounds such as thymol and eucalyptol in a mixture of methyl salicylate, benzoic acid and boric acid and phenol, 3. natural extracts (flavor oils) known to possess antimicrobial properties, and 4. sanguinarine extract, alone or in combination with zinc chloride, or zinc chloride alone.

It is suggested that the floss of the present invention containing these antiplaque and antigingivitis agents provides an important adjunct to the prevention and control of gingivitis when used with regular personal oral hygiene procedures and professional care.

Surprisingly, the cleaning/coating compositions released from the floss of the present invention retain good surface active properties and are able to clear the interproximal areas of some cell debris, food debris, material alba, sugars, starches and other precursors to plaque. This cleaning is obtained with minimal foaming while simultaneously coating the interproximal surfaces with a thin neutral film containing the flavorants of the composition. This neutral film is not metabolizable by resident oral cavity microorganisms.

By contrast, natural film formers such as lecithin-containing substances and fats are known to form anti-attachment films on mouth surfaces but these films are not suitable for the purposes of the present invention since they are metabolizable and are not neutral. Most of these naturally occurring coating substances support biological activity rather than form non-supportive inert films and as such, work opposite of the suitable film formers of the present invention. See for example: Menaker, "The Biologic Basis of Dental Caries", Chapter 16; Gibbons and Hoote, "Ann. Rev. of Microbiol" 29, pg. 19–44; and Hayes, "J. Dent. Res" 632, pg. 2–5 (1984).

As long as this transient inert coating of the present invention remains, it:

1. restricts the subsequent adherence of plaque forming materials to the teeth, thus continuing the disruption of plaque formation;

2. continues to impart a "smooth" feeling to the mouth, and 3. prolongs the flavor perception after flossing. The method of treating the oral cavity with such floss is described in our application Ser. No. 270,162, filed Nov. 14, 1988, the disclosure of which is incorporated by reference. These features are described in various Examples below. The prolonged flavor perception, described as a "clean, brushed feeling" between the teeth, is particularly novel and unexpected and makes flossing a more pleasant experience.

Most users of the floss of the present invention perceive a quite different feeling in the mouth than is perceived with typical flosses. For example, 1. The treated floss slides comfortably between teeth producing less pain, especially between "tight" teeth, and desensitizing agents reduce discomfort normally encountered with sensitive or bleeding gums.

2. The treated floss releases the compositions of the invention onto surfaces of teeth and gums more effectively cleaning the interproximal sites.

3. The released compositions condition teeth and gums and leave the mouth feeling exceptionally clean and smooth. The surfaces of the teeth are smoother and shiny. The prolonged flavor perception is generally described as "freshness" and is stronger, more natural tasting and persists much longer with the released compositions of the present invention than when state-of-the-art, encapsulated "flavored" flosses are used under comparable conditions.

Frequency of cleansing is encouraged by unique characteristics of the present invention. These cause the user to return to the invention regularly, stimulated as much by the pleasant experience as by conscious recall of "my mouth needs flossing". These characteristics are: the product is exceptionally pleasant to use. The various flavors and conditioners in the compositions of the present invention are formulated to be as pleasant as a good quality candy mint and to contribute this pleasant taste over a longer-than-expected time period thus enhancing the "its working" perception without negative "dirty mouth" connotations due to the bad taste of released plaque and debris. The latter is found to reduce frequency of use and undermine the regular cleansing advantage. The feeling in the mouth is equally pleasant. A smooth, tingly "something's happening" feeling is perceived immediately upon flossing, followed by a clean, fresh, well lubricated mouth and teeth surfaces which unexpectedly persists much longer than mints, gums, breath fresheners and even mouth washes and toothpastes. Suprisingly, the inner teeth surfaces adjacent to gum tissue also feel clean and fresh. A phenomena perceived by most consumers only after gentle phophylaxis by a dentist.

Research shows that it is not unreasonable for a typical user of the instant floss to use about 18 inches/use and to carry the dispenser in pocket or purse for use after snacks or meals.

The high flavor levels which can be pleasantly incorporated into the floss of the present invention, contribute to the plaque controlling properties of this invention. For example, natural and synthetic flavor and sweetner agents as diverse as menthol, xylitol and glycyrrhizin are known to be beneficial towards plaque control and are included in the compositions of this invention (Reference: Segal, "J. Pharrm. Sci" 74 pg 79–81 (1985) and Makkinen, "J. AM Dent. Assoc III" pg. 740–741).

In addition to the cleaning/coating compositions described above, preferred embodiments of the present invention use various viscosity control agents to impart certain viscosity characteristics to the products of the invention. It is believed that in these preferred embodiments of the invention, viscosity plays a role in achieving optimum mouth feel and flavor retention characteristics of the invention.

Viscosity control agents which are known in the food and consumer products, and not commonly used in floss, can be selected from natural and synthetic gums such as: carragenan, gum tragacanth, methyl celluloses and derivatives there of such as hydroxyethyl methyl cellulose, polyvinyl pyrrolidone, and hydrophylic carboxyvinyl polymers such as those sold under the trademark Carbopol 934. Generally, about 0.01 percent to about 10 percent of one or more viscosity control agents is used, see Table I. Often these substances are used as dry powders directly incorporated as a third phase into the melt-emulsion mixture. With appropriate control of the active water content, some or all of these dry viscosity agents could be substituted with pre-gelled viscosofiers containing no free water.

In addition to the cleaning and coating compositions described above, a preferred embodiment of the invention includes various solid, insoluble, particulates to:

1. further control viscosity of the melt-emulsion during manufacturing,
2. modify the solid texture of the completed product,
3. impart beneficial and pleasant mouth feel properties to the product which are perceived during use, and
4. optimize cleaning.

These particulates include appropriately sized calcium carbonate, talc, silica and dicalcium phosphate. These are described in Table IV below. Most of these are used as dental abrasives. In addition to these abrasives other particulates imparting beneficial properties include salts which are generally insoluble in the compositions of the invention such as tetra sodium pyrophosphate, tetra potassium pyrophosphate and sodium bicarbonate.

In addition to the stabilizers, viscosity particulates, flavoring and pH buffering ingredients; the compositions of the invention can optionally contain at least one humectant selected from the group consisting of glycerine, xylitol, sorbitol, hydrogenated glucose syrup and propylene glycol. Generally, such humectants are utilized in the proportion of about 0.1 percent to about 25 percent by weight based upon the total weight of the composition. Preferably, the humectant is utilized in an amount of about 3 to 15 percent by weight, see Examples below.

Flavors, colorants, sweetners, non-cariogenic sugars and humectants are also used to impart optimum cosmetic characteristics to the compositions of the present invention.

Generally, the flavoring component is present as an oil, emulsified into the composition by the surfactant component.

The conventional flavoring components are exemplified by the following materials, menthol, anise oil, benzaldehyde, bitter almond oil, camphor, cedar leaf oil, cinnamic aldehyde, cinnamon oil, citronella oil, clove oil, eucalyptol, heliotropine, lavendar oil, mustard oil, peppermint oil, phenyl salicylate, pine oil, pine needle oil, rosemary oil, sassafras oil, spearmint oil, thyme oil, thymol, wintergreen oil, lemon and orange oils, vanillin, spice extracts and other flavoring oils generally regarded as safe (GRAS) by health authorities.

Additional adjuvants can be added to provide color, flavor, or sweetening effects, as desired. Examples of suitable sweetening agents include sorbitol, sodium cyclamate, saccharine, commercial materials such as Nutrasweet brand of aspartame and xylitol. Citric acid or acetic acid is often utilized as a flavor additive. All types of flavoring materials are generally used in amounts of about 1.0 to about 20 percent by weight, preferably about 2.0 percent to about 15 percent by weight.

A buffering ingredient may also be added to the compositions of the invention in order to prevent natural degradation of the flavoring components or therapeutically active ingredients. Generally, the pH of these compositions is adjusted from about 3.5 to about 8, depending on the chemistry of the active ingredient most requiring protection. The buffering ingredients such as an alkali metal salt of a weak organic acid, for instance, sodium benzoate, sodium citrate, sodium phosphate, sodium bicarbonate or potassium tartrate is generally added in an amount of about 0.1 to about 1.0 percent by weight. Other buffering agents such as weak organic acids or salts of weak bases and strong acids such as boric acid, citric acid, ammonium chloride, etc can also be used in similar concentrations.

Stabilizers are often added to the compositions for additional control, such as:

a. sodium benzoate, sodium or potassium sorbate, methyl paraben, propylparaben and others approved for ingestion.

b. chemical oxidative control substances, such as ethylene-diaminetetraacetic acid, BHA, BHT, propyl gallate and similar substances approved for ingestion. Concentration levels of these stabilizers comply with industry and regulatory standards.

Successful loading of the compositions of the invention into the multi-strand dental floss requires unique manufacturing processes other than those presently used to "wax" or "flavor" commercial flosses. For example, processes used for the addition of microencapsulated flavor substances, "flavor oils" or wax to floss do not provide for the quantity of load required for the present invention nor the "controlled release" of this loaded material interproximally during flossing. Those processes used for waxing, for example, primarily coat the outer surfaces of the bundle of floss strands.

In contrast, the compositions of the invention are loaded inside the floss in concentrations ranging from about 10% to about 100% by weight of the floss. This translates to from between about 10 mg and about 100 mg per yard of floss. These loaded substances are then controllably released into the oral cavity during flossing at from between about 10 and about 80% of the load. For example, a floss containing 40 mg/yd of load will release between about 20 and about 32 mg of load during flossing. Note, the rate of release of these loaded actives is easily controlled by varying the floss construction, the process of loading, and the composition of the loaded material, providing additional novelty and utility to the present invention.

It is critical for the purposes of the present invention that much of this "loading" be accomplished in the interstitial spaces of the floss as distinguished from simply "coating" the outer surfaces of the bundle of floss strands. Much of what is called "inpregnation" in prior floss art is, upon careful examination, primarily "coating". Thus, the pressures and forces encountered during flossing allow for the loaded material to be progressively released interproximally between the teeth and under the gum line. This "interstitial loading" is particularly critical in order to avoid "stripping" the floss of actives while the floss is being inserted between the teeth and to avoid transferring major quantities of loaded materials to the fingers during flossing.

As the floss is worked through the contact point and moved gently under the gumline the loaded substances of the invention are continually released into those areas where plaque and debris are difficult to clean and where irritation bleeding and bacterial infection tend to occur.

In addition to interstitial loading a "secondary dusting" of the surface of the treated floss may be desired. This post addition of dry powder effects the "hand" of the loaded floss and makes some floss easier to hold onto during flossing. The post added compositions include abrasives etc which can contribute to the efficacy of the floss. These substances are generally added at the rate of between about 0.08 mg and about 9.0 mg per yard of floss and preferably between about 1.0 mg and about 2.0 mg per 1 yard of floss.

This loading process is described in our copending application entitled METHOD AND APPARATUS FOR ADDING CHEMOTHERAPEUTIC AGENTS TO DENTAL FLOSS, Attorney Docket No. 38,343, filed 14 November 1988, the disclosure of which is hereby incorporated herein by reference.

Unexpectedly, the construction of dental floss, that is the method used to twist the fibers into the finished floss, has been observed to influence the amount of the compositions of the invention that can be loaded into the interstitial spaces around the fibers. For example in Table I, different floss constructions are described which show variations in load of up to about 400%. In Examples A–E the composition and the method of loading were held constant while the floss construction was varied. Specifically the composition described as Example 39 in Table IV was loaded into the various flosses by the method described in our application Ser. No. 270,562, filed 14 Nov. 1988, the disclosure of which is incorporated by reference.

TABLE I

| EXAMPLE | FLOSS CONSTRUCTION (all ends 140/68) | TWIST/INCH | LOAD IN MG/ 25yds OF FLOSS |
|---|---|---|---|
| A | One blue end twisted around a core prepared by simultaneously twisting two pairs of two white ends previously twisted with one white single end. | 2 | 430 |
| B | Three white ends previously twisted at 1 twist/inch combined with two white and one blue end previously twisted at one twist/inch. | 2 | 500 |
| C | One blue end around a core of two white ends twisted with blue end under lower tension. This in turn twisted around a core of three white previously twisted. The wrap around (blue containing) twist again under lower tension. again | 2 | 1750 |
| D | Three ends twistd simultaneously. Each end comprised of two green ends previously twisted. Post dying left thread "fluffy" with many broken filaments. | 1½ | 1000 |
| E | Two ends twisted; each comprised of three white ends previously twisted at 1½ twist per inch. | 1½ | 600 |

In Examples 1 thru 4 various compositions of the invention were loaded into flosses of various construction and chemical makeup. The loading was done by dipping the floss into an agitated bath containing these compositions. The loaded floss was then hung in the air til cool and tested. The results are discussed in Table II below. Note, in all of these examples the surfactant used was PLURONIC F127, the coating composition, Dow Corning Silicone 1500, the flavor IFF 101. There was no subsequent powder treatment of the floss in these examples.

In Examples 5 thru 8 various compositions of the invention were loaded into flosses of various constructions and chemical makeup. The loading was done by passing the floss under tension and across fiber spreading devices, in an agitated bath containing these compositions. The loaded floss was then passed through a chamber charged with carrageenan, wherein the chamber was fitted with rubber plugs provided with slits which serve to remove excess powder. The loaded floss with the post added powder was then tested. Note in all these Examples the surfactant used was Pluronic F 127, the coating composition Dow Corning Silicone 1500, the Flavor IFF 101. Carrageenan was included in the loading composition in all examples. The results are set out in Table III below.

TABLE II

| | LOADING COMPOSITION | | | | | |
|---|---|---|---|---|---|---|
| EXAMPLE | SURFACTANT/ SILICONE in g. | GLYCERINE/ SACCHARIN in g. | FLAVOR(ml)/ SORBITOL in g. | OTHER ADDITIVES in g | FLOSS TYPE | RESULTS |
| 1 | 2.5/5.5 | 0/.2 | 2/0 | — | Bonded nylon | Useable, slightly oily feel |
| 2 | 25.2/10.6 | 0/1.8 | 5/1 | 0.3 methocel K4M | Bonded nylon | Useable, some separation on standing |
| 3 | 7.2/11.5 | 0/1. | 3.5/14 | 0.1 methocel K4M | Bonded nylon | Useable, too much |

TABLE II-continued

| EXAMPLE | LOADING COMPOSITION | | | | FLOSS TYPE | RESULTS |
| | SURFACTANT/ SILICONE in g. | GLYCERINE/ SACCHARIN in g. | FLAVOR(ml)/ SORBITOL in g. | OTHER ADDITIVES in g | | |
|---|---|---|---|---|---|---|
| 4 | 10.8/7.2 | 0/1. | 3.5/2 | 0.1 methocel K4M powder | Bonded nylon | silicone for optimal cleaning Useable, better than (3) |

TABLE III

| EXAMPLE | LOADING COMPOSITION | | | | FLOSS TYPE | RESULTS |
| | SURFACTANT/ SILICONE in g. | GLYCERINE/ SACCHARIN in g. | FLAVOR (ml) SORBITOL in g. | OTHER ADDITIVES in g | | |
|---|---|---|---|---|---|---|
| 5 | 10.8/7.2 | 0/1. | 3.5/2 | Carrageenan 0.5 (pre-gelled) | Unwaxed nylon | Dusting dramatically improves mouth feel |
| 6 | 15.8/7.2 | 0/1. | 8/2 | Carrageenan 5 powder | Unwaxed nylon | Improves mouth feel |
| 7 | 39.7/16.8 | 0/2.66 | 19.6/4.7 | Carrageenan 1.77 pre gelled plus powder to dry | Unwaxed nylon | Note in loading there was a single pass thru the chamber. Load was 250 mg/25 yd dry to touch. |
| 8 | 39.7/16.8 | —/2.66 | 19.6/4.7 | Carrageenan 1.77 pre gelled plus powder to dry | Oriented polyester 150/68/4 | Load was 2000mg/25 yd Dry to touch. |

In Examples 9 thru 39 various compositions of the invention were loaded into a white nylon unbonded floss constructed from 6 strands of 140 denier × 64 filiments. The loading was done by passing the floss thru a bath of the compositions of the invention maintained at about 210° F. The bath is provided with floss fiber spreading means and the floss is passed through the bath at speeds ranging from between about 1 and about 20 ft/sec. Excess composition is removed using dies and squeege arrangements. The loaded floss was then passed through a chamber charged with various powder substances which are maintained in a fluid state by a circulating charge of air passed through the chamber. Note, in all these Examples the surfactant used was Pluronic F 127; the coating composition, Dow Corning Silicone 1500; the flavor IFF 101. In these Examples there was no glycerin added. The results are described in Table IV below.

Note: these post added powders can include: dicalcium phosphate, carrageenan, Methocel K4M, silica, sodium pyrophosphate, potassium pyrophosphate and similar powdered substances which can improve the hand and/or feel of the treated floss.

TABLE IV

| EX-AM-PLE | SURFACTANT SILICONE in g. | SACCHARIN in g. | LOADING COMPOSITION FLAVOR (ml) SORBITOL in g. | METHOCEL K4M in g. | CARRAGEENAN in g. | DICALCIUM PHOSPHATE in g. | POWDER TREATMENT DICALCIUM PHOSPHATE | CARRAG-EENAN | METHOCEL K4M | RESULTS |
|---|---|---|---|---|---|---|---|---|---|---|
| 9 | 40/15 | 2.5 | 19.5/5 | — | 18 | — | | | | |
| 10 | 50/15 | 2. | 10/5 | — | 18 | — | | | + | |
| 11 | 50/15 | 2. | 10/5 | — | 18 | — | | + | | |
| 12 | 50/15 | 2. | 10/5 | — | 18 | — | + + | | | |
| 13 | 50/15 | 2. | 10/5 | — | 18 | — | + + | | + + | |
| 14 | 60/10 | 2.5 | 15/10 | — | 2.5 | — | | + + | + + | Each version of this series had useful but different properties. Loads ranged from between about 500 to 700 mg/25 yd. |
| 15 | 60/10 | 2.5 | 15/10 | — | 2.5 | — | + | | + | |
| 16 | 60/10 | 2.5 | 15/10 | 13 | 2.5 | — | + | | + + | |
| 17 | 40/15 | 2.0 | 15/15 | — | — | 15 | + | | | |
| 18 | 50/15 | 2.5 | 10/7.5 | — | — | 15 | + | + | + + | |
| 19 | 50/15 | 2.5 | 10/7.5 | — | — | 15 | + | | | |
| 20 | 50/15 | 2.5 | 10/7.5 | — | — | 15 | + | | + + | |
| 21 | 50/15 | 2.5 | 10/7.5 | — | 17.5 | — | + + | | | |
| 22 | 50/15 | 2.5 | 10/0 | — | 17.5 | — | + + | + | | Load was 500 mg/25 yd |
| 23 | 50/20 | 2.5 | 10/0 | — | 17.5 | — | + | + | | Load was 600 mg/25 yd |
| 24 | 50/20 | 2.5 | 10/0 | — | 17.5 | — | | + | | Good mouth feel |
| 25 | 50/20 | 2.5 | 10/0 | 18 | — | — | | | | Crystals of xylitol formed in finished product, coliquid effect in mouth. |
| 26 | 50/15 | 2. | 10/5 | 18 | — | — | | | | Improved mouth feel |
| 27 | 45/18.5 | 1.8 | 14/4.5 | 16.2 | — | — | | + | | Improved mouth feel |
| 28 | 50/20 | 2.5 | 13.75/ xylitol 30 | — | — | — | + | + | | Powder improves mouth feel |
| 29 | 50/15 | 2. | 10/Lycasin powder 10 | — | 8 | — | | | | |
| 30 | 50/15 | 2. | 12.5/7.5 | — | 8 | — | | | | |
| 31 | 45/17.5 | 2.25 | 12.5/7.5 | 6.5 | — | 8.75 | + | + | | |
| 32 | 45/17.5 | 2.25 | 12.5/7.5 | 6.5 | — | 8.75 | + + | + | | Loaded 800 mg/25 yd dicalcium phosphate improves cleaning perception, carrageenan improves mouth feel. |
| 33 | 47.2/20 | 2. | 10/3.75 | 12.5 | — | 4.5 | + + | + | | |
| 34 | 47.2/20 | 2. | 10/3.75 | 12.5 | — | 4.5 | + | + | | |
| 35 | 50/20 | 2.5 | 10/0 | — | 15 | 15 | + | + | | Loaded 800 mg/25 yd Best of this group |
| 36 | 200/80 | 10 | IFF 343 Acid Grape 45/100 | — | — | — | | + | Silica instead of methocel | Sorbitol makes product different from #45 and very useful. (pH controlled at 3.5 with citrate buffer) Addition of silica improves cleaning perception. |
| 37 | 160/70 | 10 | IFF 343 Acid Grape 45/100 | — | — | Silica 50 | | + | Silica instead of methocel | |
| 38 | 50/20 | 2.5 | 10 | — | 15 | 15 | + | + | | Propyl gallate (0.05%) and BHA (0.05%) added to stabilize. Flavor improves |

TABLE IV-continued

| EXAMPLE | SURFACTANT SILICONE in g. | LOADING COMPOSITION | | | | | POWDER TREATMENT | | | RESULTS |
| | | SACCHARIN in g. | SORBITOL in g. | FLAVOR (ml) METHOCEL K4M in g. | CARRAGEENAN in g. | DICALCIUM PHOSPHATE in g. | DICALCIUM PHOSPHATE | CARRAGEENAN | METHOCEL K4M | |
| --- | --- | --- | --- | --- | --- | --- | --- | --- | --- | --- |
| 39 | 50/20 | 2.5 | 10 | | 15 | 15 | + | + | | but yellows on storage at 104° F. Propyl gallate (0.1%) and EDTA (0.2%) added to stabilize Flavor and color stable after 7 months at 104° F. |

Various cleaning and coating compositions suitable for use in the various flosses of the invention are described in illustrative Examples 40 thru 48 in Table V below. All percentages listed are by weight.

plished in a single pass, the result of either being that between about 10 mg and about 100 mg of the preparation is loaded into each yard of the floss.
In addition:

TABLE V

| EXAMPLE | CLEANER (%) | COATING COMPOSITION (%) | SORBITOL (%) | CARRAGEENAN VISCOSIFIER (%) | DICALCIUM PHOSPHATE DENTAL ABRASIVE (%) | FLAVOR (%) |
|---|---|---|---|---|---|---|
| 40 | PEG Stearate 40 | Silicone glycol/20 | 10 | 10 | 15 | 5 |
| 41 | Sodium lauryl sulfate/20 | Carbowax/10 | 20 | 20 | 20 | 10 |
| 42 | Tween-80/30 | Dodecane/10 | 30 | 10 | 10 | 10 |
| 43 | PEG Stearate/20 | Carbowax/10 | 20 | 15 | 25 | 10 |
| 44 | Sodium lauryl sulfate/25 | Dodecane/15 | 25 | 10 | 15 | 10 |
| 45 | Tween-80/40 15 | Silicone glycol/10 | 15 | 15 | 13 | 7 |
| 47 | Sodium lauryl sulfate/15 | Silicone glycol/15 | 30 | 15 | 15 | 10 |
| 48 | Tween-80/20 | Carbowax/20 | 20 | 15 | 15 | 10 |

Various cleaning and coating compositions suitable for incorporation of various biological actives into the various flosses of the invention are described in illustrative Examples 49 to 57 in Table VI. Unless otherwise indicated all units are in percent.

a. the excess load can be removed from the outer surface of the floss, and
b. solid particulate can be added to the outer surface of the floss.

In most instances, standard bobbin winding proce-

TABLE VI

| | | | INCORPORATION OF VARIOUS BIOLOGICAL ACTIVES | | | | | |
|---|---|---|---|---|---|---|---|---|
| EXAMPLE | SURFACTANT F 127 | SILICONE 1500 | CARRAGEENAN | FLAVOR | SACCHARIN | EDTA/PROPYL GALLATE | POLYOL OR ABRASIVE | BIOLOGICAL ACTIVE |
| 49 | 42.75 | 14.25 | 15 | 10.7 | 2 | 0.2/0.1 | silica (10) | tetra sodium pyrophosphate (5) |
| 50 | 45 | 15 | 15 | 5.0 | 3 | 0.2/0.1 | dicalcium phosphate (15) | menthol (0.1) thymo (0.2) eucalyptol (0.2) boric acid 90.5) methyl salicylate (0.2) |
| 51 | 55.5 | 18.5 | — | 9.0 | 1 | 0.2/0.1 | sorbitol (15) | cetylpyrinium chloride (0.1) |
| 52 | 42.75 | 14.25 | 15 | 10 | 2.4 | 0/0.1 | silica (15) | zinc chloride (0.5) |
| 53 | 42.75 | 14.25 | 10 | 10 | 2.9 | 0/0.1 | silica (10) | strontium chloride (desensitizer) (10) |
| 54 | 42.75 | 14.25 | 15 | 10 | 2.5 | — | dicalcium phosphate (15) | metrinidizol (0.5) |
| 55 | 42.75 | 14.25 | 15 | 10 | 2.8 | — | sorbitol (15) | sanguinarine extract (0.2) |
| 56 | 42.75 | 14.25 | 9.6 | 2.4 | — | sorbitol | polymyxin B sulfate (15) | (1000 units/gram) |
| 57 | 39.5 | 13.0 | 15 | 10 | 2.2 | 0.2/0.1 | silica (15) | potassium nitrate (desensitizer) (5) |

The method of manufacturing the various dental flosses described in our application Ser. Nos. 270,163, 270,723, 270,132, 270,167 and 270,135 all filed 14, Nov. 1988, the disclosures of which are incorporated by reference requires that the floss fibers in each instance be twisted into a floss construction which is suitable for receiving the various loads and for releasing substantial portions of this load during flossing.

The manufacturing method includes:
a. Spreading the floss fibers,
b. loading the preparation in a molten state between the spread floss fibers,
c. reforming the spread fibers back to the initial twist, and
d. repeating steps a–c repetitively, or
e. supplying sufficient mechanical and hydraulic pressure so that a–c above can be effectively accomplished in a single pass, the result of either being dures can be used to package most of these loaded flosses. Where the floss load contains a therapeutic substance that has a history of instability, unit packaging of the floss, preferably in 18 inch to 36 inch pieces may be required; such unit packaging can incorporate water and oxygen barrier materials as required.

The effect that twisting of the floss fibers has on the load capacity of the floss is illustrated in Table I. In a preferred embodiment of the invention the twisting described in Table I is achieved with a Galvani Twister Model 8S.

Various spreading means can be used to separate the floss bundle of fibers into a ribbon of fibers preferably and approximately one layer thick.

For the purposes of the present invention these fiber spreading means can include:
1. passing the floss over flat surfaces under tension,
2. passing the floss thru a series of ladder guides,
3. passing the floss through a compressing means such as nip rollers, and/or
4. the use of comb like means through which the fibers are drawn, preferably untwisted.

Various means can be used to introduce the load into the spread fibers including:
1. Immersing the spread fibers into a bath containing the material to be loaded (generally this bath is at elevated temperature and the load is characterized as a melt-emulsion. Usually, the loaded floss is then passed through a compression means exerting considerable hydraulic force to further force the load into the interstitial spaces. Extended cooling may be required.
2. Containing the material to be loaded between the rollers in a nip roller arrangement, or
3. Pumping the material to be loaded into the floss that has been separated and heated.

In most loading methods the load material is under pressure either in its entirety or instantly at the point of critical contact with the spread fibers.

Some preferred means used to introduce the preparation to be loaded into the floss are described in detail below.

If the active to be loaded is sensitive to heat; a controlled melt at-point-of-contact system can be used to provide a limited residence time where the active in the melt is at elevated temperature. This can be achieved in the heated pump/vortex mixing arrangement described below; with or without a separate heating of the floss prior to loading. In a preferred embodiment, this loading step is carried out under substantially water-free conditions.

This invention will be further understood but not limited by reference to the drawings included herewith wherein:

It will be obvious to one skilled in the art that the individual elements illustrated in FIGS. 1–4 can be reassembled in a variety of units to spread the floss and load the actives interstitially, there by affording the manufacturer full freedom to optimize the process for preferred production speeds, scale efficiencies, various loading levels and to accomodate a wide range of active substances.

Figure 5:
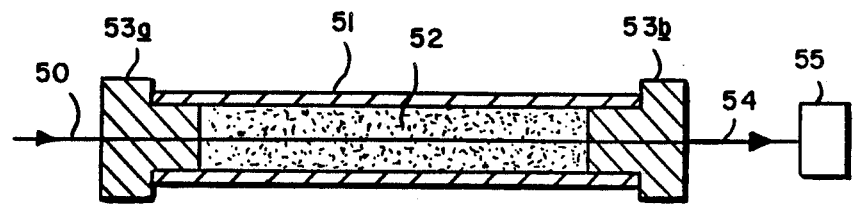
Figure 6:
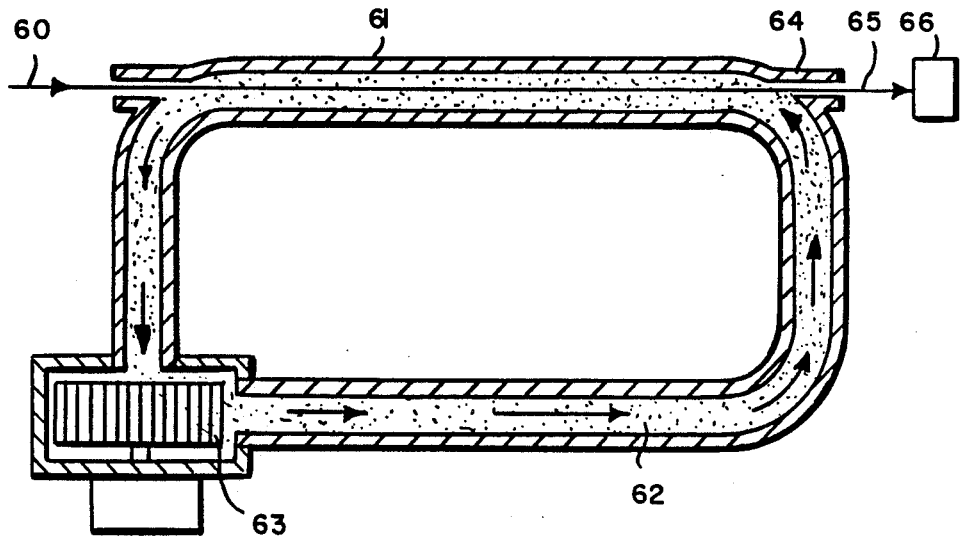

FIGS. 5 and 6 are cross sectional schematics of various powder loading means which may be used in a secondary process to add particulate substances to the surfaces of the loaded floss.

The process of loading multi-strand floss with various preparations described above will be further understood by the following detailed description of specific embodiments of the invention.

Figure 1:
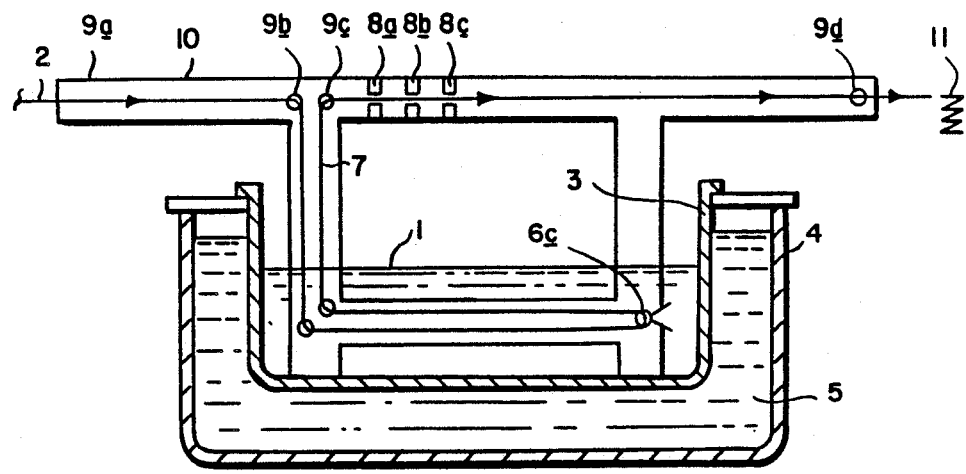
FIG. 1. Is a cross sectional view of a schemetic bath loading system, wherein the floss is passed over flat surfaces under tension to open up the floss. Some of these surfaces are immersed in a bath of the preparation being loaded followed by passing the floss through a compressing means.

Referring to FIG. 1, the preparation 1, to be loaded into the untreated floss 2, is maintained in a liquid state in vessel 3 by means of bath means 4 which is provided with bath oil 5. Various preparations suitable for use in this bath means are described in Table II above.

The floss is passed over a series of flat surfaces 6a, 6b, and 6c, in the bath under tension. This opens floss 2, and allows preparation 1 to enter the space around the floss fibers at surfaces 6a, 6b, and 6c. Loaded floss, 7, is then passed through compressing means 8a, 8b, and 8c, inorder to remove excess preparation 1, from the outside of floss 7 and to further force preparation 1 into the spaces around the fibers of loaded floss 7. Various floss guide means 9a, 9b, 9c, and 9d, are located throughout floss guide frame 10, to assist in pulling the floss under tension, over surfaces 6a thru 6c and thru compressing means 8a thru 8c.

Temperatures of oil 5, in bath 4, are sufficient to maintain preparation 1 in a molten state. Tension and a pulling force is applied to untreated floss 2, and loaded floss 7, by means of a driven take-up means 11, which passes the floss thru the system at rates from between about 1 and about 20 ft/sec.

Compressing means 8a, 8b and 8c, can be a steel die with a prescribed aperture equal to the expanded diameter of treated floss 7, and/or an elastomeric squeegy means with similar apertures. The function of compressing means 8a thru 8c is to wipe excess preparation 1 from floss 7 and to further force preparation 1 into interstitial spaces of treated floss 7.

Figure 2:
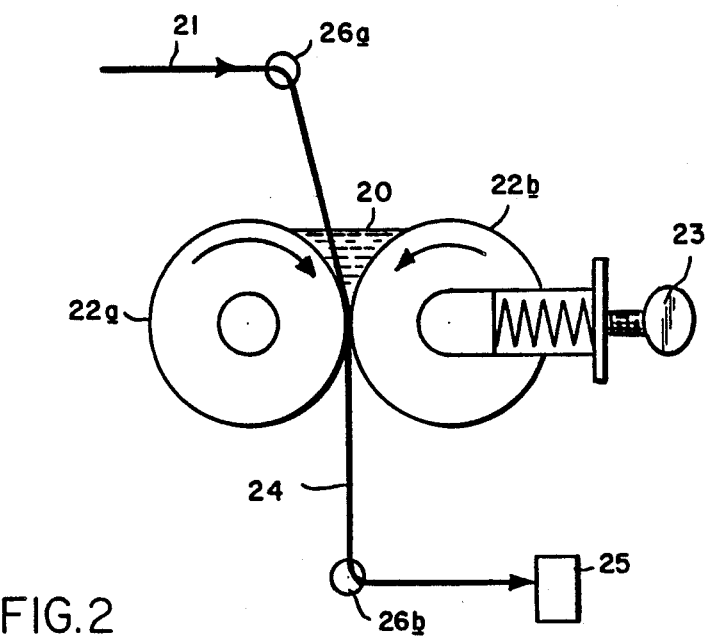
FIG. 2. Is a cross sectional view of a schematic compressing loading means, wherein the floss is passed through a bath contiguous with a compressing rollers means.

Referring to FIG. 2, the liquid preparation 20, to be loaded into untreated floss 21, is maintained between heated nip roller means 22a and 22b. Nip roller 22b, is provided with adjustable tension means 23, which controls the compression on floss 21, while avoiding damage to the floss fibers during loading. These nip rollers provide some of the pulling force and impart sufficient tension to spread floss 21 during the compressing/loading step. Loaded floss 24, is wound on take up means 25.

The compression force obtained with the nip rollers is sufficient to load substantial quantities of preparation 20, i.e. from about 8 to about 80 mg/yd as the floss is passed through this system at speeds between 2 and 20 ft/sec. Six to 10 ft/sec is a convenient speed. Various guides 26a and 26b, are positioned to assist and guide floss 21 through the system.

Generally, preparations 20 are maintained in a molten state at temperatures ranging from between about 180° F. and about 350° F. By controlling the viscosity of preparations 20, the flow of these preparations into nip rollers 22a and 22b can be maintained.

Preparations suitable for loading include those set out in Tables II thru VI.

Figure 3:
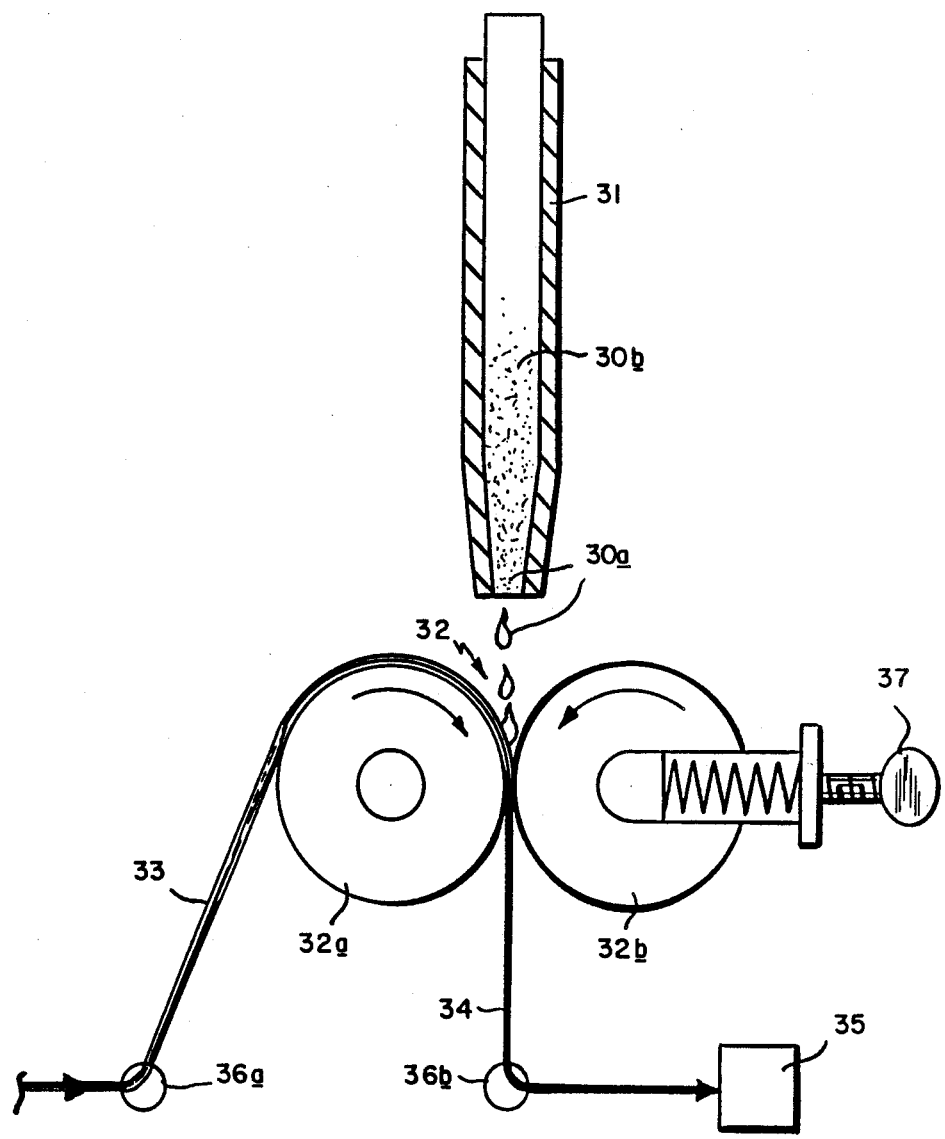
FIG. 3. Is a cross sectional view of a schematic compressing loading means, wherein the floss is passed through compressing rollers along with the preparation to be loaded which is introduced to the floss immediately prior to entering the compressing means.

Referring to FIG. 3 the liquid preparation 30a, is heated in tip applicator 31 which liquifies solid preparation 30b. Liquid preparation 30a is metered onto compressing means 32 comprising heated nip rollers 32a and 32b.

Untreated floss 33, passes over nip rollers 32a, and is compressed by nip roller 32b, while liquid preparation 30a, is forced between the fibers of floss 33. Treated floss 34, is then wound onto take up means 35. Various floss guides 36a and 36b are positioned to assist the travel of floss 33 and guide untreated floss 33 and treated floss 34 through the system.

Nip roller 32b, is provided with adjustble tension means 37, which controls the compression force applied to floss 33, while avoiding physical damage to the floss fibers during loading of preparation 30a.

Solid preparation 30b, is maintained as a melt 30a, by maintaining the temperature in tip applicator 31, at approximately 310° F. Rate of application of preparation 30a is approximately 1.85 g/min. The quantity of preparation 30a loaded into floss 33 is controlled by:
1. the flow rate of liquid preparation 30a from applicator 31,
2. the speed of nip rollers 32a and 32b,
3. nip roller 32b tension, as determined by the adjustment of tension means 37,
4. the preparation and viscosity of liquid preparation 30a, and
5. the construction and twist of floss 33.

When the preparation of Example 39 in Table IV was applied at a speed of 13 ft/sec. a load of 180 mg/25 yd was obtained in floss 34; whereas when loaded at a rate of 6.5 ft/sec. a load of 450 mg/25 yd was obtained. In contrast, when the melt flow rate of 30a was increased to 4.0 g/min, the loaded floss 34 contained 340 mg/25 yd at a speed of 13 ft/sec.

Preparations suitable for loading include the Examples set out in Tables II thru VI.

Figure 4:
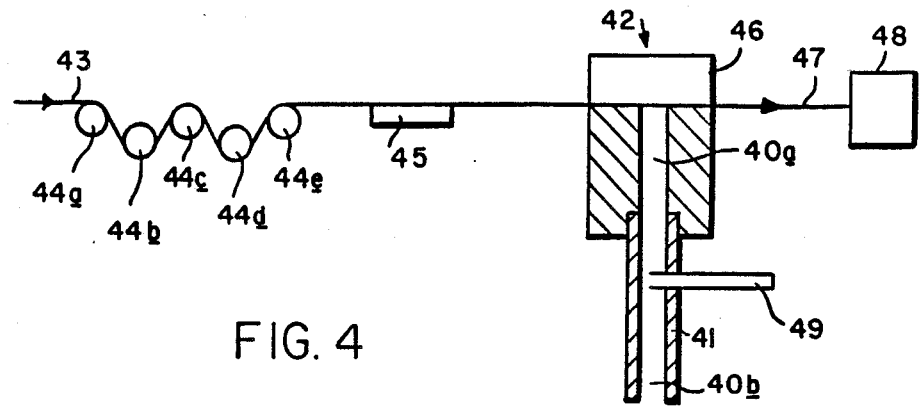
FIG. 4. Is a cross sectional view of a schematic of a liquid loading means, wherein the floss is passed through ladder guide tension means, preheated and then the preparation to be added is forced into the spread floss fibers by a pump/applicator means.

Referring to FIG. 4, liquid preparation 40a, is heated in pump applicator 41, which liquefies solid preparation 40b. Liquid preparation 40a is then metered under pressure into heated ceramic chamer 42.

Untreated floss 43, is passed over ladder guide/tensioning means 44a, 44b, 44c, 44d and 44e, and then over floss pre-heater means 45. The heated, untreated floss 43, is then passed thru heated ceramic chamber 42, where liquid preparation 40a, is pumped around the various separated floss fibers in charging area 46. Treated floss 47, is wound onto take up reel 48.

Pump applicator 41, can be fitted with a vortex mixing means so that various heat sensitive substances such as antimicrobials can be introduced via line 49, into preparation 40a, with a minimum dwell time prior to the floss charging step. Where dwell time is critical to the stability of the preparation to be loaded the process of FIG. 4 is preferred.

Referring to FIG. 5, powder charging of the various flosses loaded as shown in FIGS. 1 thru 4 can be achieved by passing the loaded floss 50 into powder charging chamber 51, loaded with powder particulate 52. Powder charging chamber 51, is provided with elastomeric plugs 53a and 53b, containing slots to compress the floss and wipe off excess powder particulate 52.

Referring to FIG. 6 the treated floss 60, is passed into powder charging loop chamber 61, which is charged with circulating powder particulate 62. Chamber 61, is provided with circulator fan 63, and with sealing means 64. Powdered treated floss 65, is wound on floss take up means 66.

As noted above, these post added powder particulate substances can include dicalcium phosphate, carrageenan, Methocel K4M, silica, sodium pyrophosphate potassium pyrophosphate and similar powdered substances which can improve the hand and/or feel of the treated floss. The addition of such powder particulate substances is described in Table IV above.

As noted previously, most of this loading of the floss in the method of the present invention takes place in the interstitial spaces around the fibers. The loaded substances are trapped in these spaces as the fibers are spread apart and these substances introduced. After loading, the stressed fibers tend to return to their original shape with the entrapped substances held in the interstitial spaces. This loaded floss exhibits a larger diameter due to the entrappment of the load compared to the same floss unloaded. The presence of the load is discernible on a cross section inspection and/or by dyeing the load which is then evident interstitially.

The pressures and forces encountered during flossing result in the loaded material being progressively, released interproximally; between the teeth and under the gum line. This "interstitial loading" is particularly critical inorder to avoid "stripping" the floss of actives while the floss is being inserted interproximally. As the floss is worked through the contact point and moved gently under the gumline the loaded substances of the invention are continually released into those areas where plaque and debris are difficult to clean and where irritation bleeding and bacterial infection tend to occur.

The interstitial loading of various compositions by the method of the present invention into the multistrand dental floss requires unique manufacturing processes other than those presently used to "wax" or "flavor" commercial flosses. For example, processes used for the addition to the floss of microencapsulated flavor substances, "flavor oils" or wax do not provide for the quantity of load achieved by the present invention nor the "controlled release" of this loaded material interproximally during flossing. Those processes used for waxing, for example, primarily coat the outer surfaces of the bundle of floss strands.

In contrast, the various compositions loaded by the process of the present invention into the floss range from about 10 mg to about 80 mg/yd of the floss. These loaded substances are then controllably released into the oral cavity during flossing at from between about 10 and about 80 percent by weight of the load. For example, a floss containing 40 mg/yd of load will release between about 20 and about 32 mg/yd of load during flossing. As noted above, the rate of release of these loaded actives is controlled by the floss construction, the process of loading, and the preparation of the loaded material.

The "load" of the various preparations with the process of the invention into the interstitial spaces between floss fibers also provides a suitable process for loading the various therapeutic substances to the interproximal sites. From between about 5 and about 60 percent by weight of the load can be comprised of these therapeutic substances described in our application Ser. Nos. 270,163, 270,723, 270,132, 270,167 and 270,135, all filed 14 Nov. 1988, the disclosures of which are incorporated by reference.

Therapeutic substances that can be added to the floss as antiplaque/antigingivitis agents include:
a. antiplaque and antitartar substances such as the pyrophoshates and zinc chloride,
b. first generation antimicrobial agents which are antibacterial agents such as oxygenating compounds, quaternary ammonium compounds, phenolic compounds and plant alkaloids such as sanguinarine, c. organo-iodine salts, d. second generation antimicrobial agents which are antibacterial agents with substantivity such as chlorhexidine, (chlorhexidine gluconate), alexidine, octenidine, stannous fluoride and sodium fluoride, and e. antibiotics include penicillin, tetracycline, polymixin B, vancomycin, kanamycin, erythromycin, niddamycin, metronidazole and spiromycin.

Antimicrobial agents with antiplaque and anti gingivitis efficacy may be classified according to their substantivity. While first generation agents exhibit little substantivity, second generation agents are characterized by high substantivity. These second generation agents are capable of not only reducing plaque accumulation but also of preventing the development of gingival inflammation by 70–90% when used once or twice daily. In contrast, first generation agents are generally not capable of preventing gingivitis unless they are used from 4 to 6 times a day, since they do not seem to reduce plaque below the individual threshold for disease. The first generation agents suitable for use in the method of the present invention include:

1. quaternary ammonium compounds such as benzethonium chloride, cetylpyridinium chloride, 2. phenolic compounds such as thymol and eucalyptol in a mixture of methyl salicylate, benzoic acid and boric acid and phenol, and 3. sanguinarine extract, usually in combination with zinc chloride.

Preferred second generation agents include stannous fluoride and chlorhexidine. Both of these substances are introduced into the preparation for loading by specific processing of various components of the preparation. These and the organo-iodine salts are described in detail in our application Ser. Nos. 270,163, 270,723, 270,132, 270,167 and 270,135 all filed 14 Nov. 1988, the disclosures of which are incorporated by reference.

In addition to interstitial loading a "secondary dusting" of the surface of the treated floss may be desired. This post addition of dry powder effects the "hand" of the loaded floss and makes some floss easier to hold onto during flossing. The post added compositions include abrasives etc. discussed in Table IV above which can contribute to the efficacy of the floss. These substances are generally added at the rate of between about 0.8 mg and about 9.0 mg per yard of floss and preferably between about 1 mg and about 2 mg/yd of floss.

The various floss construction types described in Table I were processed according to the method and apparatus generally described in FIG. 2 and post treated with powder generally as described in FIG. 6. The dramatic effect of floss construction on loading the preparations of the invention are set forth in Table VII. The release rate of these loaded preparations were similar to those described previously.

What we claim is:

1. A method of adding a chemotherapeutic preparation to a multi fiber dental floss wherein: the preparation comprises:

a. a surfactant selected from the group consisting of: sodium lauryl sulfate, sodium lauroyl sarcosinate, polyethylene glycol stearate, polyethylene glycol monostearate, coconut monoglyceride sulfonates, sodium alkyl sulfates, sodium alkyl sulfoacetates, block copolymers of polyoxyethylene and polyoxybutylene, allylpolyglycol ether carboxylates, polyethylene derivatives of sorbitan esters, propoxylated cetyl alcohol, block copolymers comprising a cogeneric mixture of conjugated polyoxybutylene and polyoxylethylene compounds having as a hydrophobe a polyoxybutylene polymer of at least 1200 molecular weight, soap powder, and mixtures thereof, and b. a coating substance insoluble in said surfactant selected from the group consisting of: silicones, silicone glycol co-polymers, polydimethyl siloxanes, long chain hydrocarbons, normal paraffins having a chain length of 16 carbon atoms or greater, paraffins with several loci of branching and unsaturation and carbowaxes, and the method comprises, repetitively:

a. spreading said floss fibers, b. introducing said preparations in a molten state into the spaces around said fibers, and c. returning said fibers to their preload twist, such that from between about 10 and about 80 mg of said preparation are contained in one yard of said floss in a releasable state.

2. A method of adding a chemotherapeutic preparation to dental floss according to claim 1 wherein said preparation is loaded into the floss at a rate between about 10 mg/yd and about 100 mg/yd.

3. A method of adding a chemotherapeutic preparation to dental floss according to claim 1 wherein said preparation is released during flossing at a rate between about 10% and about 80% by weight of said load.

4. A method of adding a chemotherapeutic preparation to dental floss according to claim 1 wherein said floss is multi fiber, multifilament with a denier between about 300 and about 1200.

5. A method of adding a chemotherapeutic preparation to floss according to claim 1 wherein the floss contains between about 100 and about 800 filaments.

6. A method of adding a chemotherapeutic preparation to floss according to claim 1 wherein said preparation is insoluble in said floss and contained in the interstitial spaces between the fibers of said floss such that up to 80% by weight is released from said floss during flossing.

7. A method of adding a chemotherapeutic preparation to floss according to claim 1 wherein said preparation is loaded into the floss at a rate between about 20 and about 50 mg/yd and wherein said preparation re-

TABLE VII

| Example | Floss Construction Ref to Example in Table I | Floss Dry Wt. g/25 yds | Floss Loaded Wt. g/25 yds | Load Wt. mg/ 25 yds |
|---|---|---|---|---|
| 58 | A | 2.47 | 3.08 | 610 |
| 59 | B | 2.47 | 3.45 | 980 |
| 60 | C | 2.26 | 4.34 | 2080 |
| 61 | D | 2.40 | 3.32 | 920 |
| 62 | E | 2.20 | 3.45 | 1250 | leases at a rate between about 30% and about 70% by weight of the load.

8. A method according to claim 1 wherein the preparation contains an antimicrobial selected from the goup consisting of stannous fluoride, chlorhexidine, organo-iodine salts and mixtures thereof.

9. A method according to claim 1 wherein spreading of the fibers is achieved by passing the floss over a series of flat surfaces under tension.

10. A method according to claim 1 wherein said spreading of the fibers is achieved by compressing the floss.

11. A method according to claim 10 wherein the compressing is achieved with nip rollers and the preparation is forced between the fibers by the hydraulyic pressure generated by said nip rollers.

12. A method according to claim 1 wherein the fibers are spread by a ladder guide means, preheated, and the preparation to be added is heated and forced under pressure between said fibers.

13. A method according to claim 1 wherein the preparation is introduced into the spread floss fibers by means of a heated tip applicator means.

14. A method according to claim 1 wherein the preparation is introduced into the spread floss fibers by means of a heated pump applicator and ceramic chamber means.

15. A method according to claim 14 wherein the pump applicator is provided with vortex mixing means to accommodate the addition of heat sensitive antimicrobials.

16. A method according to claim 1 wherein the floss containing the chemotherapeutic preparation is passed through a powder charging means at a rate sufficient to load between about 0.8 and about 9.0 mg/yd of powder onto the floss.

17. A method according to claim 1 wherein the addition of the chemotherapeutic preparation is performed under substantially water-free conditions.

* * * * *